US00PP26580P3

(12) United States Plant Patent

Olesen et al.

(10) Patent No.: US PP26,580 P3

(45) Date of Patent: Apr. 5, 2016

(54) *CLEMATIS* PLANT NAMED 'EVIPO035'

(50) Latin Name: *Clematis viticella*
Varietal Denomination: Evipo035

(71) Applicants: Mogens Nyegaard Olesen, Fredensborg (DK); Raymond Evison, St. Sampsons (GB)

(72) Inventors: Mogens Nyegaard Olesen, Fredensborg (DK); Raymond Evison, St. Sampsons (GB)

(73) Assignee: POULSEN ROSER A/S, Fredensborg (DK)

( * ) Notice: Subject to any disclaimer, the term of this patent is extended or adjusted under 35 U.S.C. 154(b) by 242 days.

(21) Appl. No.: 13/986,924

(22) Filed: Jun. 14, 2013

(65) Prior Publication Data

US 2014/0373232 P1 Dec. 18, 2014

(51) Int. Cl.
*A01H 5/00* (2006.01)
*A01H 5/02* (2006.01)

(52) U.S. Cl.
USPC ..... Plt./228
CPC ..... *A01H 5/02* (2013.01)

(58) Field of Classification Search
USPC ..... Plt./228
See application file for complete search history.

(56) References Cited

PUBLICATIONS http://mygarden.rhs.org.uk/blogs/graham_rice/archive/2010/07/08/new-clematis-at-hampton-court.aspx.*

* cited by examiner

*Primary Examiner* — Annette Para

(57) ABSTRACT

A new *Clematis* plant with a compact growth habit, profuse, violet flowers, and continuous summer flowering. The variety successfully propagates from softwood cuttings and is suitable for cultivation commercial nursery culture. This new and distinct variety has shown to be uniform and stable in the resulting generations from asexual propagation from vegetative cuttings.

3 Drawing Sheets

Botanical classification: Genus: *Clematis*. Species: *viticella*.

Variety denomination: 'Evipo035'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling The two parents were crossed during the summer of 1994 and the resulting seeds were planted the following winter in a controlled environment in Guernsey, Channel Islands. The new variety named 'Evipo035' originated as a single seedling from the stated cross.

The new *clematis* plant may be distinguished from its female seed parent and male pollen parent primarily by flower color and growth habit.

The objective of the hybridization of this *clematis* plant was to create a new and distinct variety for nursery culture with unique qualities such as:

1. Uniform and abundant violet flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo035' was selected by Mogens N. Olesen and Raymond J. Evison in their *clematis* development program in the Channel Islands, United Kingdom in 1995. Asexual reproduction of 'Evipo035' by means of vegetative cuttings and traditional layering was first performed by Mogens N. Olesen and Raymond J. Evison in the nursery during the summer of 1995. This initial and subsequent asexual propagations have demonstrated that the characteristics of 'Evipo035' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo035'.

Specifically illustrated in the FIG. 1 are open flowers, stems, and leaves.

Figure 1:
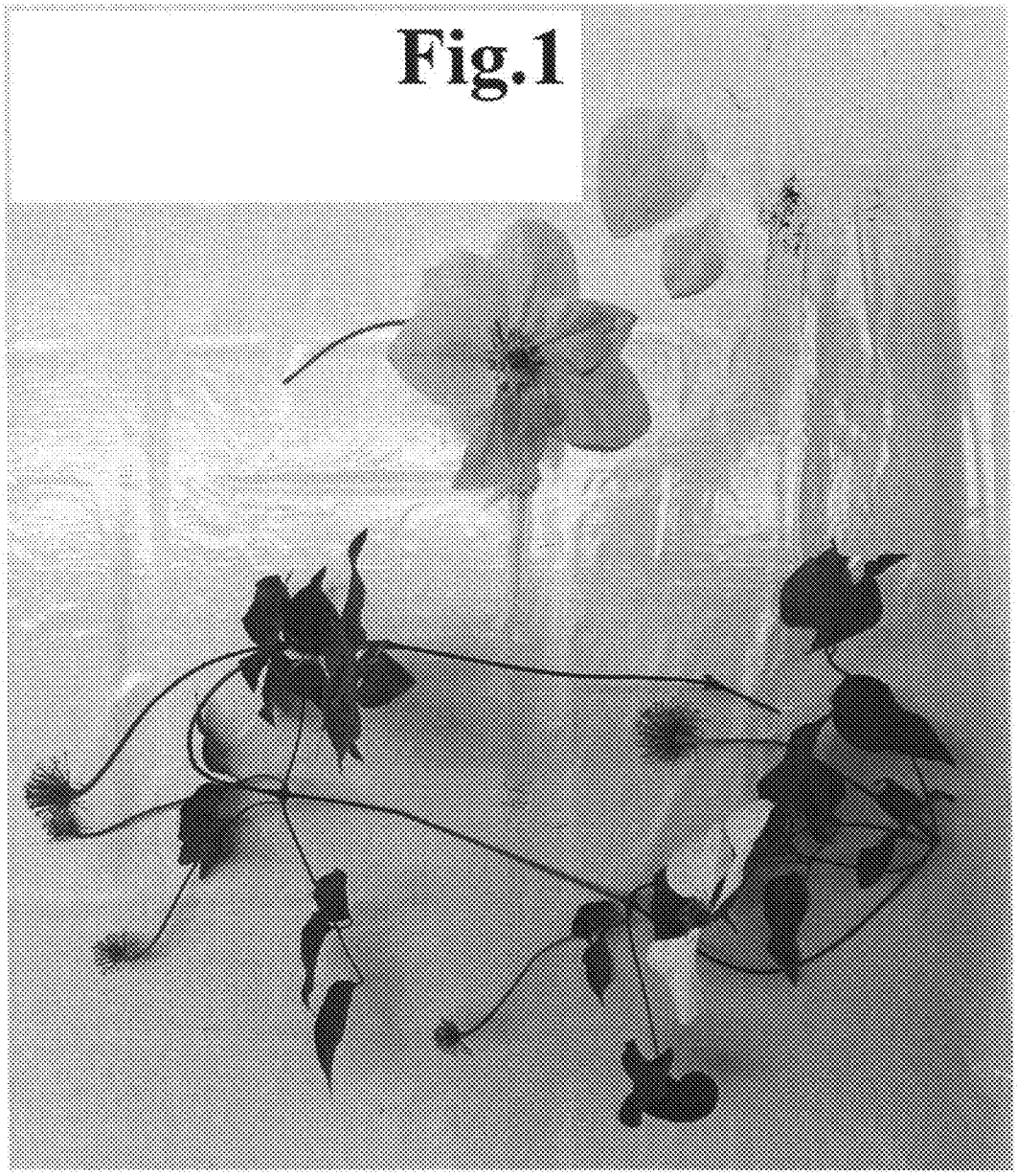
Figure 2:
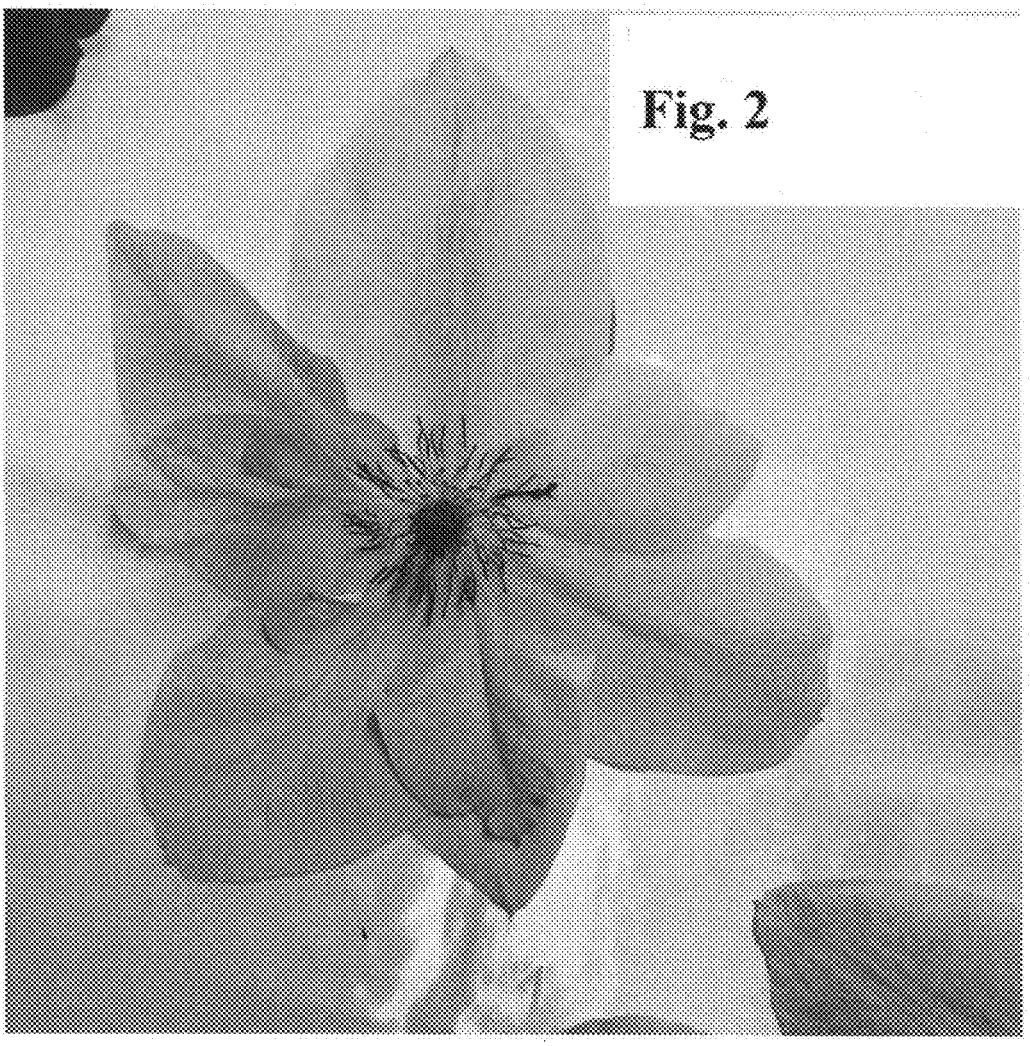

Illustrated in FIG. 2 is an open flower close up.

Figure 3:
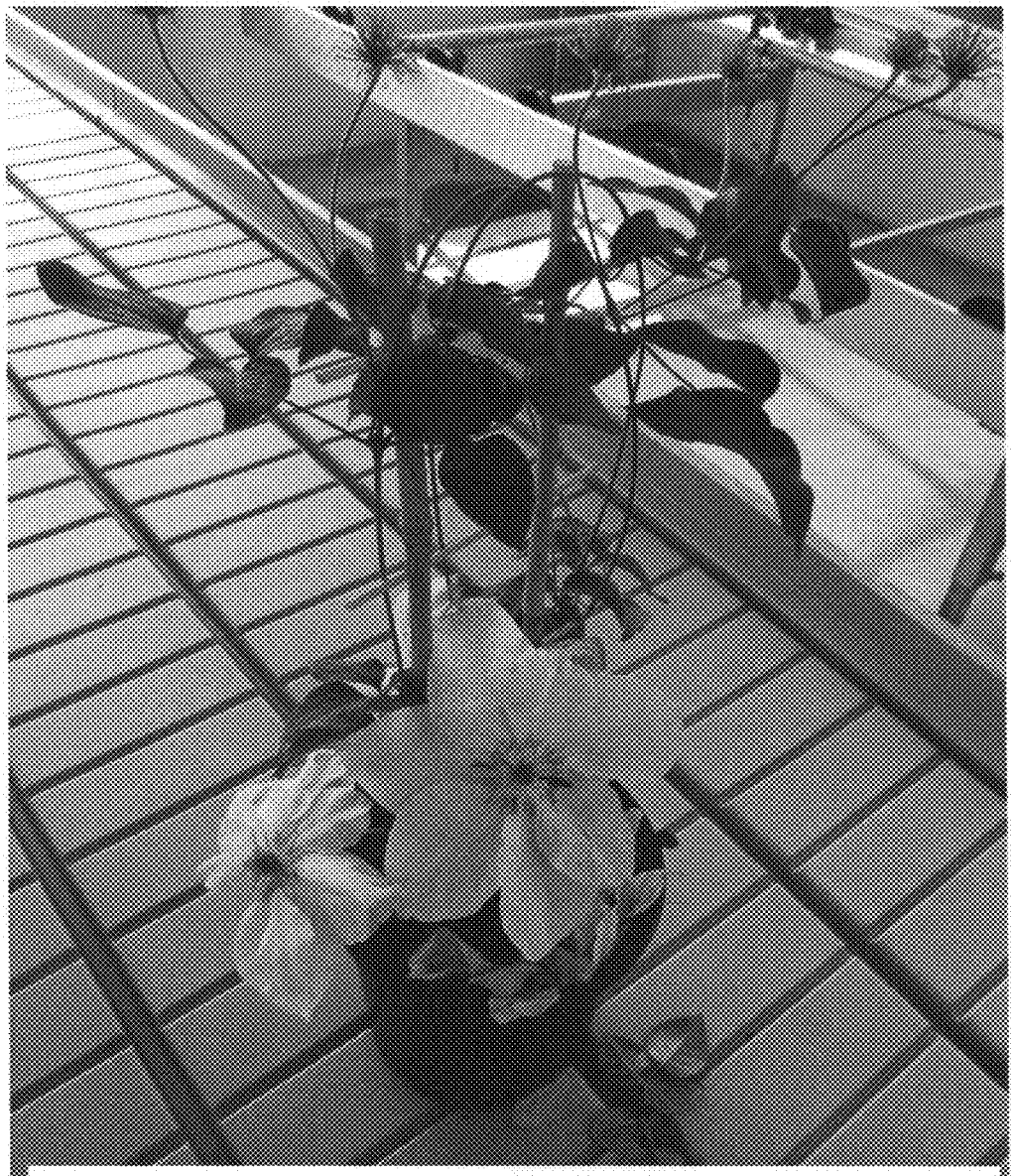

Illustrated in FIG. 3 is the entire plant growing in a container.

DETAILED DESCRIPTION OF THE VARIETY

The following is a detailed description of 'Evipo035', as observed in its growth throughout the flowering period in glasshouses in Denmark. Observed plants were cultivated for a period of 18 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo023' described and illustrated in U.S. Plant Pat. No. 15,166 are compared to 'Evipo035' in Chart 1.

CHART 1

| | 'Evipo035' | 'Evipo023' |
|---|---|---|
| Flower diameter | 140 mm | 90 mm-120 mm |
| Tepal color, upper surface | Violet Blue Group 91C | Violet Blue 91A |
| Tepal count | 11 | 6 to 8 |

Flower and Flower Bud

Blooming habit: Continuous. The natural flowering period is generally from April to September.

Peduncle:

*Surface texture.*—Smooth and pubescent.

*Length.*—On average 40 mm.

*Color.*—Yellow-Green Group 144D.

*Strength.*—Moderately strong.

Receptacle: Absent.

Flower arrangement:

*Location on vine.*—New growth only.

*Borne.*—Normally in clusters of 2 flowers.

Flower bloom:

*Size.*—On average, flowers are 140 mm in diameter and 15 mm in depth.

*Profile.*—Open flowers are flat.

*Fragrance.*—None.

*Lasting quality.*—Flowers normally remain 5 days on the plant.

Tepals:

*Tepal color.*—Upon and after opening the upper surface is Violet Blue Group 91C. The lower surface is Violet Blue Group 91D.

*Quantity.*—Normally 11 tepals.

*Size.*—50 to 70 mm in length by 30 to 50 mm wide.

*Shape.*—Individual tepal shape is obovate to elliptic. The tepal apex is rounded, somewhat mucronate. The tepal base is acute.

*Apex recurvature.*—None.

*Tepal cross section.*—Flat.

*Margins.*—Entire.

*Persistence.*—Tepals drop off cleanly.

Reproductive organs:

*Pollen.*—Not observed.

*Anthers.*—Size: 4 mm in length. Color: Violet Group 83A. Quantity: On average, 40.

*Filaments.*—Color: White Group 155B. Length: 9 mm.

*Pistils.*—Quantity: On average, 65.

*Stigmas.*—Inferior in location relative to the length of the filaments and the height of the anthers.

*Styles.*—Color: Violet Group 83A. Length: 5 mm.

Plant

Plant form: Climbing.

Plant growth: Vigorous.

Size: Seasons growth attains 100 cm in height. Average spread is 100 cm.

Hardiness: Trials to date show the variety hardy in USDA Zones 6.

Stems:

*Color.*—Juvenile stems are Yellow-Green Group 144B. Mature stems are Greyed-Orange Group 175B.

*Internodes.*—On average, 15 cm between nodes.

*Length.*—Normally 50 cm from the base of the plant to the flowering portion of the stem.

*Diameter.*—Normally 2 mm.

*Texture.*—Mature stems are generally ribbed. Young stems are smooth.

Plant foliage:

*Leaf characteristics.*—Deciduous.

*Arrangement.*—Triternate.

*Leaf size.*—Compound leaves are normally 120 mm (l)× 80 mm (w). Leaflets are normally 50 mm (l)×30 mm (w).

*Abundance.*—On average 2 leaves per 10 cm of stem.

*Leaf color.*—Juvenile upper & lower are Yellow-Green Group 144A. Mature upper Yellow-Green Group 147A. Mature lower Yellow-Green Group 146A.

*Stipules.*—Absent.

*Petioles.*—Size: Normally 80 mm in length by 1 mm diameter. Texture: Smooth. Color: Greyed-Purple Group 183D.

*Petioloule.*—Size: Normally 10 to 40 mm in length by 1 mm diameter. Texture: Smooth. Color: Greyed-Purple Group 183B.

*Leaflet shape.*—Generally lanceolate. The base is cordate. The apex is acute.

*Margin.*—Entire.

*Surface.*—The upper and lower side is smooth.

*Thickness.*—Moderate.

*Glossiness.*—Not glossy.

Disease resistance: Subject to any disease that normally attacks the species. However the variety is more tolerant to *clematis* wilt than some *clematis*.

Cold hardiness: The variety is tolerant to USDA Hardiness Zone 6.

Heat tolerance: The variety has been found to be suitable for climate conditions found in the American Horticulture Society heat zone 7.

The invention claimed is:

1. A new and distinct variety of *clematis* plant named 'Evipo035', substantially as described and illustrated, due to its abundant violet flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *